(12) United States Patent
Behnke, II et al.

(10) Patent No.: US 9,259,268 B2
(45) Date of Patent: Feb. 16, 2016

(54) VESSEL SEALING USING MICROWAVE ENERGY

(75) Inventors: Robert J. Behnke, II, Erie, CO (US); Scott E. M. Frushour, Boulder, CO (US); Jeffrey L. Jensen, Boulder, CO (US); Wayne L. Moul, Loveland, CO (US)

(73) Assignee: Covidien LP, Mansfield, MA (US)

( * ) Notice: Subject to any disclaimer, the term of this patent is extended or adjusted under 35 U.S.C. 154(b) by 784 days.

(21) Appl. No.: 13/312,172

(22) Filed: Dec. 6, 2011

(65) Prior Publication Data

US 2013/0144284 A1    Jun. 6, 2013

(51) Int. Cl.
*A61B 18/18*    (2006.01)
*A61B 18/00*    (2006.01)
*A61B 17/29*    (2006.01)

(52) U.S. Cl.
CPC ............. *A61B 18/1815* (2013.01); *A61B 17/29* (2013.01); *A61B 2018/0016* (2013.01); *A61B 2018/0063* (2013.01); *A61B 2018/00404* (2013.01); *A61B 2018/00559* (2013.01); *A61B 2018/00791* (2013.01); *A61B 2018/00875* (2013.01); *A61B 2018/183* (2013.01)

(58) Field of Classification Search
CPC .................................................. A61B 18/1815
USPC ............................................... 606/41, 50–51
See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |

(Continued)

FOREIGN PATENT DOCUMENTS

| | | |
|---|---|---|
| CN | 101534738 A | 9/2009 |
| CN | 201299462 | 9/2009 |

(Continued)

OTHER PUBLICATIONS

International Search Report from EP Appl. No. 12179628.8 mailed Oct. 8, 2012.

(Continued)

*Primary Examiner* — Carl H Layno
*Assistant Examiner* — Jennifer Ghand

(57) ABSTRACT

An end effector assembly includes a pair of opposing jaw members movable from a first position in spaced relation relative to one another to at least one subsequent position wherein the jaw members cooperate to grasp tissue therebetween. Each of the jaw members includes a microwave antenna assembly and a shielding member including a metallic plate coupled to ground and a dielectric material. The end effector assembly also includes a splitter configured to receive an active signal from a source of microwave energy and split the active signal into a first signal transmitted to the microwave antenna assembly in one of the jaw members and a second signal transmitted in the microwave antenna assembly in the other jaw member.

15 Claims, 6 Drawing Sheets

(56) References Cited

U.S. PATENT DOCUMENTS

| | | | |
|---|---|---|---|
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| 6,224,593 B1 | 5/2001 | Ryan et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,679,882 B1 * | 1/2004 | Kornerup | 606/51 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 2008/0091189 A1 | 4/2008 | Carlton | |
| 2010/0030207 A1 | 2/2010 | Hancock | |
| 2010/0036379 A1 | 2/2010 | Prakash et al. | |
| 2010/0094271 A1 | 4/2010 | Ward et al. | |
| 2010/0249769 A1 * | 9/2010 | Nau et al. | 606/33 |
| 2011/0073594 A1 | 3/2011 | Bonn | |
| 2011/0213353 A1 | 9/2011 | Lee et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 2364660 A1 | 9/2011 |
| EP | 2457532 A1 | 5/2012 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |
| WO | WO 2012/076844 A1 | 6/2012 |

OTHER PUBLICATIONS

European Search Report from EP Appln. No. 12195454.9 mailed Mar. 27, 2013.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.

(56) References Cited

OTHER PUBLICATIONS

U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.

(56) References Cited

OTHER PUBLICATIONS

Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Chinese Office Action dated Sep. 25, 2015, issued in Chinese Application No. 201210519407.

* cited by examiner

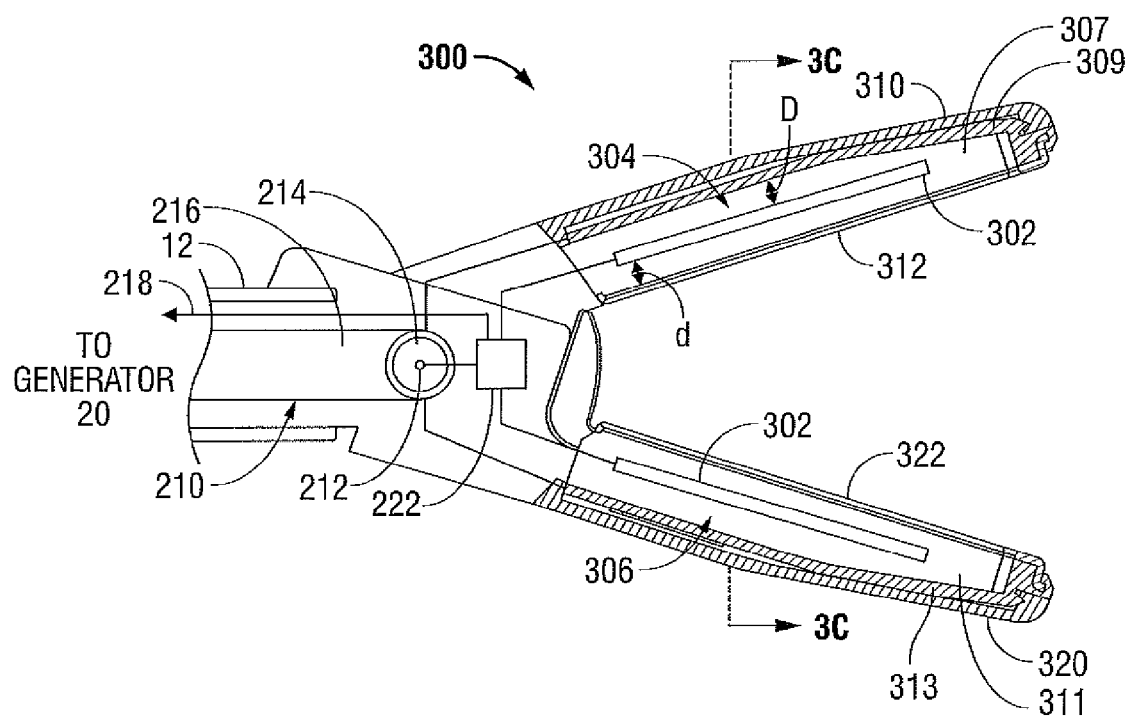
FIG. 3A
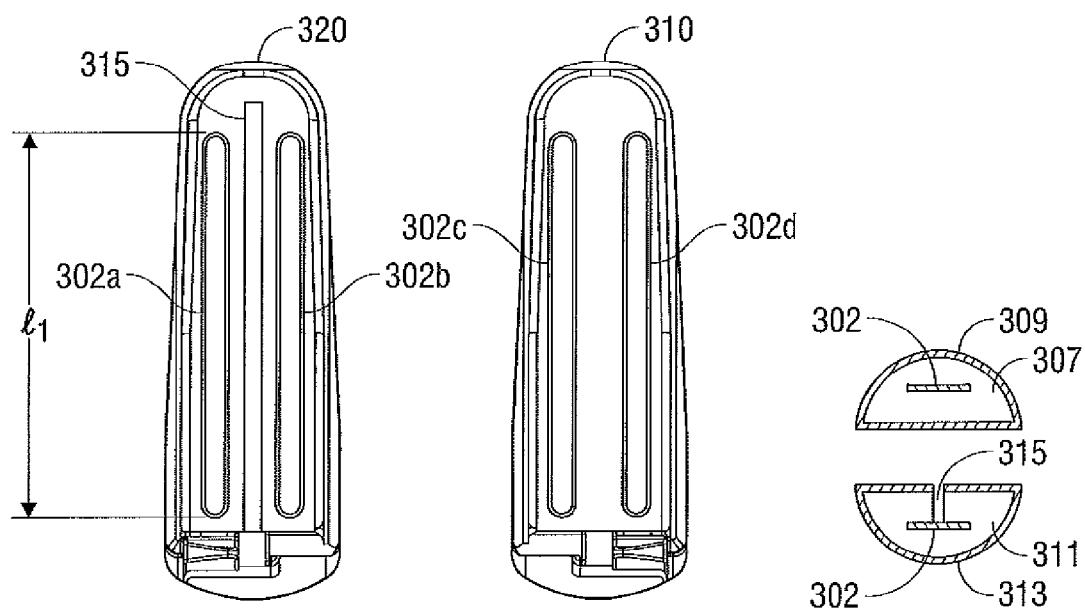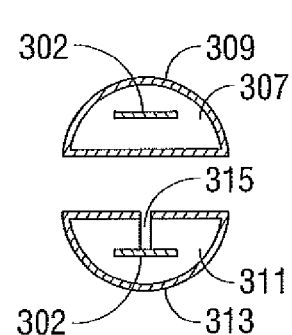
FIG. 3B  FIG. 3C

VESSEL SEALING USING MICROWAVE ENERGY

BACKGROUND

1. Technical Field

The present disclosure relates to forceps for sealing various types of tissue. More particularly, the present disclosure relates to open, laparoscopic or endoscopic forceps that utilize microwave energy to seal tissue.

2. Background of the Related Art

In many surgical procedures, body vessels, e.g., blood vessels, ducts, adhesions, fallopian tubes, etc. are sealed to defunctionalize or close the vessel. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heat processes have been employed.

A forceps is particularly useful for sealing tissue and vessels since forceps utilizes mechanical action to constrict, grasp, dissect and/or clamp tissue. Current vessel sealing procedures utilize heat treatment and sometimes pressure to heat and desiccate tissue causing closure and sealing of the body vessel. In addition, forceps allow for control of the applied pressure to the tissue. The combination of heating and applied pressure provides a uniform, controllable seal with minimum collateral damage to body tissue.

SUMMARY

As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

In an aspect of the present disclosure, an end effector assembly for microwave forceps is provided. The end effector assembly includes a pair of opposing jaw members movable from a first position in spaced relation relative to one another to at least one subsequent position wherein the jaw members cooperate to grasp tissue therebetween. Each of the jaw members includes a microwave antenna assembly and a shielding member including a metallic plate coupled to ground and a dielectric material. The end effector assembly also includes a splitter configured to receive an active signal from a source of microwave energy and split the active signal into a first signal transmitted to the microwave antenna assembly in one of the jaw members and a second signal transmitted in the microwave antenna assembly in the other jaw member.

The phase of the first signal is offset in relation to a phase of the second signal, e.g., 180°. The distal end of antenna assembly may be terminated with an open or may be shunted to ground. If the antenna assembly is terminated with an open, the length of the antenna assembly is a multiple of a half wavelength. If the antenna assembly is shunted to ground, the length of the antenna assembly is an odd multiple of a quarter wavelength.

In another aspect of the present disclosure, an end effector assembly for microwave forceps is provided. The end effector assembly includes a splitter configured to receive an active signal from a source of microwave energy and split the active signal into a first signal and a second signal. The end effector assembly also includes a pair of opposing jaw members movable from a first position in spaced relation relative to one another to at least one subsequent position wherein the jaw members cooperate to grasp tissue therebetween. Each of the jaw members includes a microwave antenna array having a first antenna and a plurality of second antennas, a shielding member including a metallic plate coupled to ground and a dielectric material, and a multiplexer configured to receive the first signal or the second signal from the splitter, wherein the multiplexer provides the first signal or the second signal to the first antenna or the first antenna and at least one of the plurality of second antennas in the microwave antenna array.

The phase of the first signal is offset in relation to a phase of the second signal, e.g., 180°. The first antenna and each of the plurality of second antennas may be terminated with an open or may be shunted to ground. If the first antenna and each of the plurality of second antennas is terminated with an open, the length of the first antenna and each of the plurality of second antennas is a multiple of a half wavelength. If the first antenna and each of the plurality of second antennas is shunted to ground, the length of the first antenna is an odd multiple of a quarter wavelength and the length of each of the plurality of second antennas is a multiple of a half wavelength.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 3A-3C are views of a microwave end effector assembly according to one embodiment of the present disclosure;

DETAILED DESCRIPTION

Figure 1:
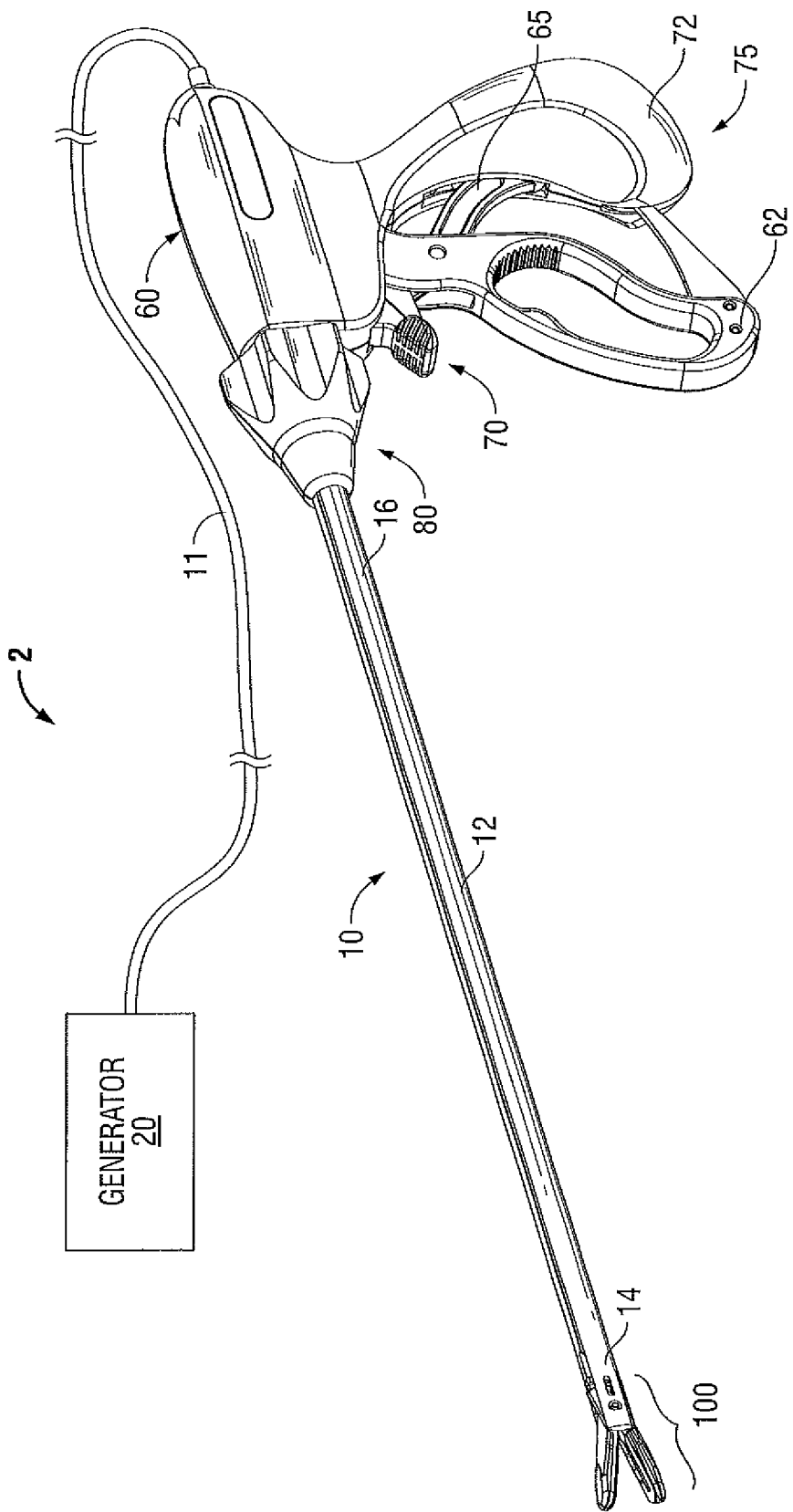
FIG. 1 is a perspective view of a tissue sealing system including a forceps and an energy generator according to one embodiment of the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to open, laparoscopic or endoscopic forceps that utilize microwave energy to seal tissue. By using microwave energy to seal tissue, tissue could desiccate faster, thereby reducing sealing times while decreasing the amount of thermal spread. The microwave energy uses a near field effect to vibrate the water molecules within the tissue against each other to generate the heat required for tissue fusion. In the embodiments described below, the electromagnetic near field may be contained and directed such that any surrounding healthy structures are not heated while the tissue disposed within the electromagnetic near field is heated.

Referring now to FIG. 1, a tissue sealing system 2 according to the present disclosure is shown including a forceps 10 coupled to a generator 20. The forceps 10 is adapted to seal tissue using microwave energy. The generator 20 may be configured to output various types of microwave energy (e.g., from about 300 MHz to about 10,000 MHz).

The forceps 10 is coupled to the generator 20 via a cable 11 adapted to transmit energy and control signals therebetween. Various embodiments of the forceps 10 utilizing the aforementioned types of energy are discussed in more detail below. Alternatively, forceps 10 may be a portable handheld device that includes an electrosurgical power source that includes a generator, a controller and a battery.

The forceps 10 is configured to support an end effector assembly 100. Forceps 10 typically includes various conventional features (e.g., a housing 60, a handle assembly 75, a rotating assembly 80, a trigger assembly 70, end effector 100) to mutually cooperate to grasp, seal and, if warranted, divide tissue. Handle assembly 75 includes moveable handle 62 and handle 72 that is integral with housing 60. Handle 62 is moveable relative to handle 72 to actuate end effector assembly 100 to grasp and treat tissue. Forceps 10 also includes a shaft 12 that has distal end 14 that mechanically engages end effector assembly 100 and proximal end 16 that mechanically engages housing 60 proximate rotating assembly 80 disposed at the distal end of housing 60. Rotating assembly 80 is mechanically associated with shaft 12. Movement of rotating assembly 80 imparts similar rotational movement to shaft 12 which, in turn, rotates end effector assembly 100.

Figure 2:
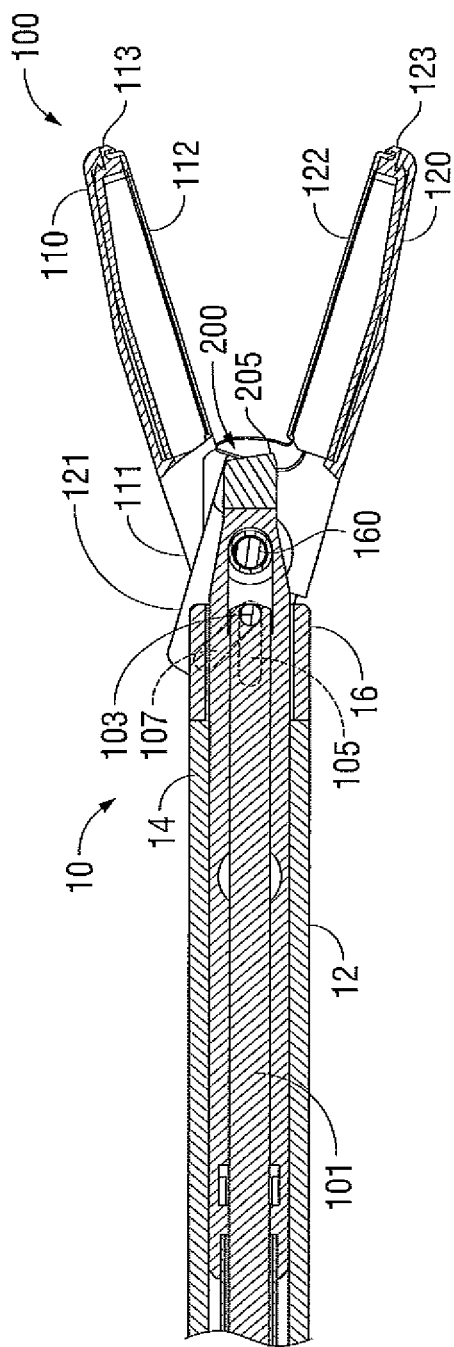
FIG. 2 is a cross-sectional view of a distal end of the forceps of FIG. 1.

Referring to FIG. 2, the end effector assembly 100 includes two jaw members 110 and 120 having proximal ends 111, 121 and distal ends 113, 123. Jaw members 110 and 120 are pivotable about a post 160 and are movable from a first position wherein jaw members 110 and 120 are spaced relative to another, to a second position wherein jaw members 110 and 120 are closed and cooperate to grasp tissue therebetween. Jaw members 110 and 120 may be unilateral or bilateral. As discussed in more detail below, the end effector assembly 100 may be adapted for use with various energy sources. Alternatively, one of the jaw members 110 and 120 may remain stationary while the other jaw members moves in relation to the stationary jaw member.

The shaft 12 houses a pushrod 101, or other suitable actuation mechanism, that is operatively coupled to the movable handle 62 such that when the handle 62 is moved relative to the handle 72 the pushrod 101 moves longitudinally, either proximally or distally within the shaft 12. The pushrod 101 includes a push pin 103 disposed at the distal end 16 of shaft 12. Each of the jaw members 110 and 120 includes a slot 105 and 107, respectively, disposed at the proximal ends thereof. The slots 105 and 107 are in mechanical cooperation with the push pin 103, which is adapted to move within the slots 105 and 107. The pin 103 and slots 105 and 107 operate as a cam-follower mechanical linkage. Motion of the pushrod 101 causes the pin 103 to slide within respective slots 105 and 107. The slots 105 and 107 may be angled with respect to the distal ends of the jaws members 110 and 120 such that the members 110 and 120 move either toward or away from each other as the pushrod 101 is moved longitudinally in a proximal or distal direction, respectively.

The forceps 10 also includes a trigger assembly 70 that advances a knife 200 (optional) disposed within the end effector assembly 100. Once a tissue seal is formed, the user activates the trigger assembly 70 to separate the tissue along the tissue seal. Knife 200 includes a sharpened edge 205 for severing the tissue held between the jaw members 110 and 120 at the tissue sealing site.

Each jaw member 110 and 120 includes a sealing surface 112 and 122, respectively, disposed on an inner-facing surface thereof. Sealing surfaces 112 and 122 cooperate to seal tissue held therebetween upon the application of microwave energy by applying a sealing pressure to the tissue. The forceps 10 determines the seal pressure on the tissue based upon various properties of the tissue disposed between the jaw members 110 and 120 including: tissue impedance, tissue type, tissue clarity, tissue compliance, temperature of the tissue or jaw members, water content in tissue, jaw opening angle, water mortality in tissue, energy delivery, jaw closure pressure, etc. Based upon such properties, the seal pressure may be determined either before, during or after electrical activation of at least one jaw member in real time during electrical activation. A pressure controller (not shown) may be operatively coupled to the shaft 12 of the forceps 10. The pressure controller may be any type of electrical, or electro-mechanical mechanism that provides additional force on the drive assembly (not shown) to increase or decrease the closure pressure of the jaw members 110 and 120 which, in turn, increases or decreases the seal pressure on the tissue disposed therebetween. For example, a servo motor, gear assembly, hydraulic mechanism, worm drive, etc. may be coupled to the shaft 12 and operatively coupled to the drive assembly (not shown) to provide additional force to the drive assembly (not shown) as per the information.

FIGS. 3A-3C illustrate a microwave end effector assembly 300 according to one embodiment of the present disclosure. The end effector assembly 300 is coupled to a coaxial cable 210 that is housed within the shaft 12 and the cable 11. The cable 210 includes an inner conductor 212 surrounded by an inner insulator 214, which is, in turn, surrounded by an outer conductor 216 (e.g., a cylindrical conducting sheath). The inner conductor 212 and outer conductor 216 may be constructed of copper, gold, stainless steel or other conductive metals with similar conductivity values. The metals may be plated with other materials, e.g., other conductive materials, to improve their properties, e.g., to improve conductivity or decrease energy loss, etc.

The end effector assembly 300 includes a microwave antenna assembly 302 having one or more microwave antennas 302a, 302b, 302c and 302d associated with sealing surfaces 312 and 322, respectively. The microwave antennas 302a-302d are electrically coupled to the generator 20, which is adapted to supply microwave energy to the forceps 10 through the cable 210. The coaxial cable 210 connects one or more of the microwave antennas 302a, 302b and 302c, 302d to an active element of the generator 20 through the inner conductor 212. Generator 20 only supplies an active signal to antennas 302a-302d when the jaw members 310 and 320 are in a closed position.

As shown in FIG. 3A, an active signal from inner conductor 212 is fed to a splitter 222. Splitter 222 receives the active signal and splits the phase of the active signal into two equal signals having a phase component that is offset by 180° from each other. Splitter 222 may split the signals using a balun, line delays, lumped elements or any other suitable electrical components that may be used to split the active signal into two signals having a phase offset 180°. Splitter 222 may be electrically coupled to generator 20 via transmission line 218. Transmission line 218 may be provided as a separate wire or may be integrated into cable 210. Generator 20 may control splitter 220 to vary the phase offset between the two split signals and/or control the method of splitting.

FIG. 3B shows a top view of the microwave antennas 302a-302d configured as longitudinal strips that extend the lengths of the sealing surfaces 312 and 322. The microwave antennas 302a-302d may be made from any type of conducting, non-reactive metals, such as stainless steel.

When tissue is sealed by the assembly 300, the antennas 302a-302d may provide for an automatic termination of the sealing procedure. As sealing progresses, the tissue separating the antennas 302a, 302b and 302c, 302d shrinks, thereby decreasing the separation between the antennas 302a, 302b and 302c, 302d. As the antennas 302a, 302b and 302c, 302d are moved toward each other by the compression forces, the microwave energy transmitted therethrough is reflected back therethrough and the radiation automatically stops due to the proximity of the microwave antenna assemblies 302 antenna (e.g., antennas 302a, 302b and 302c, 302d).

As shown in FIG. 3A, the distal end of antenna assemblies 302 are terminated in an open. In this situation, the length $l_1$ (FIG. 3B) of antennas 302a-302d is a multiple of a half wavelength (i.e., $\lambda/2$, $\lambda$, $1.5\lambda$, $2\lambda$, etc.) to help direct energy between the two active. For example, when both antenna assemblies are terminated in an open as shown in FIG. 3A and the wavelengths are $\lambda/2$, the impedance reflected back to the source looks like an open (no energy transfer between an antenna and ground). When the two antenna assemblies 302 in jaw members 310 and 320 are distanced correctly, the distance being a function of the dielectric distance "d" and the width of the tissue between jaw members 310 and 320, the impedance between antenna assemblies 302 in jaw members 310 and 320 is close to the source impedance and maximum power can be transferred between the two antenna assemblies 302.

The jaw members 310 and 320 also include shielding members 304 and 306 disposed therein, which include respective sealing surfaces 312 and 322. Each of the shielding members 304 and 306 may include a dielectric portion 307 and 311 and a metallic plate 309 and 313 disposed over the dielectric portions 307 and 311, respectively. Metallic plates 309 and 313 are coupled to outer conductor 216 and are configured to act as a ground-shield. As shown in FIG. 3C, the ground-shield can be constructed to encompass the entire electromagnetic field generated by antennas 302a-302d. As such, the ground-shield reduces stray fields from emitting outside the jaw enclosure and ensures that only the intermediate areas between antenna assemblies 302 are exposed to microwave energy. Antenna assemblies 302 may also be positioned such that shielding members 304 and 306 create a parabolic reflector to concentrate the microwave energy at distance $D_1$ or the tissue.

The dielectric portions 307 and 311 may be formed from a dielectric material that controls the impedance of the antenna assemblies 302 and act as a buffer between antennas 302a, 302b and 302c, 302d. Dielectric portions 307 and 311 may be made from ceramics (e.g., aluminum nitride (AlN) or alumina ($Al_2O_3$)), Teflon, Styrofoam, polyester foam, glass, plastic, etc. The buffering would reduce the effects of tissue dielectrics that vary when the tissue heats up and desiccates.

The distance "D" between antenna assemblies 302 and metallic plates 309 and 313 may be varied to produce different effects in the tissue grasped between the jaws. For instance, if the distance "D" were to be reduced such that antenna assemblies 302 were disposed closer to metallic plates 309 and 313, there would be higher desiccation in the tissue resulting in a cutting effect.

The shielding members 304 and 306, by nature of the dielectric properties and the presence of metallic plate 309 and 313, reflect the microwave energy from the antennas 302a-302d toward tissue being grasped between the sealing surfaces 312 and 322. This arrangement allows for use of any number of antennas 302 (e.g., a single antenna) since the microwave energy is restricted to the volume of tissue being grasped between the jaw members 310 and 320.

The end effector assembly 300 also includes a longitudinally-oriented channel 311 defined in the sealing surface 312 extending from the proximal end to the distal end thereof. The channel 315 facilitates longitudinal reciprocation of the knife 200 along a particular cutting plane to effectively and accurately separate the tissue along a formed tissue seal. The channel 315 may also be defined in the sealing surface 322 or solely disposed in only one sealing surface, e.g., sealing surface 312.

Figure 4A:
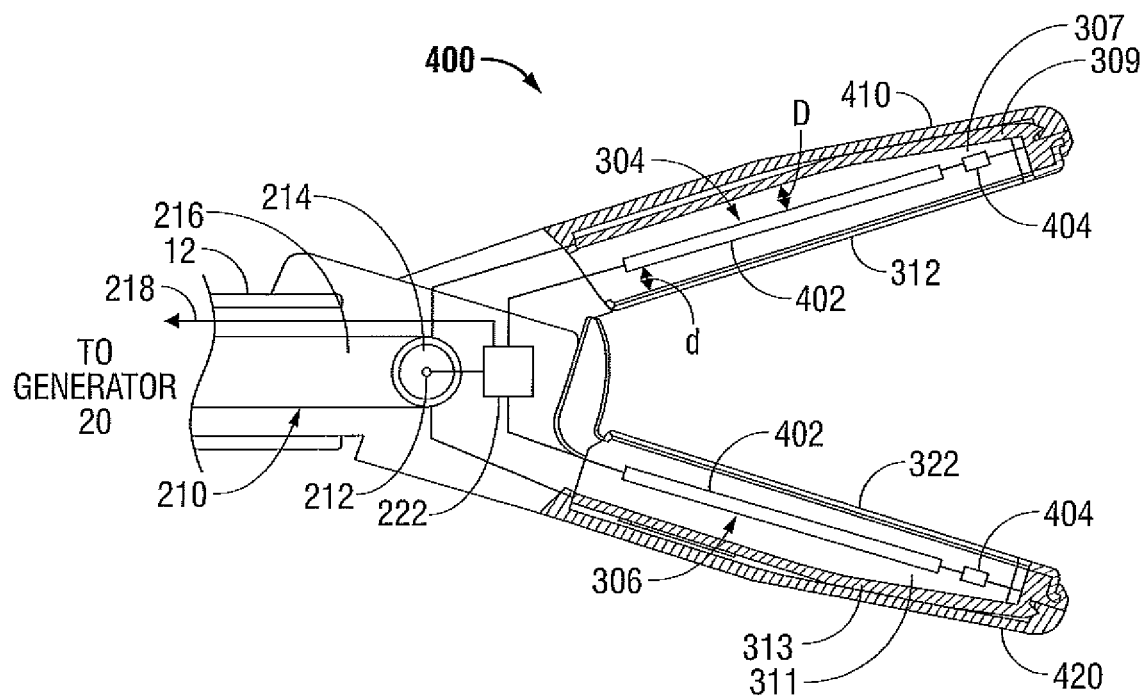
FIGS. 4A-4B are views of a microwave end effector assembly according to another embodiment of the present disclosure.
Figure 4B:
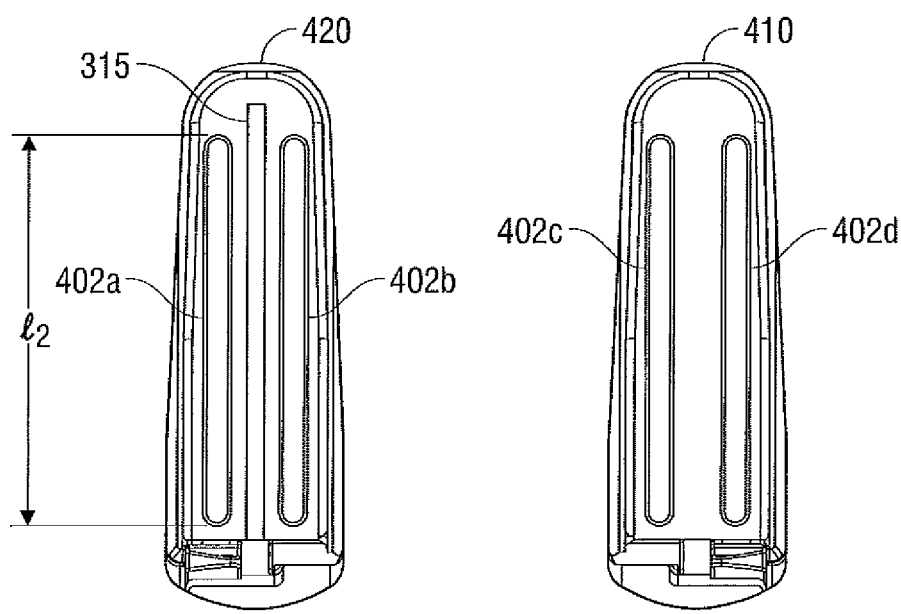

FIGS. 4A and 4B illustrate a microwave end effector assembly 400 according to another embodiment of the present disclosure. The end effector assembly 400 includes jaw members 410 and 420. Jaw members 410 and 420 include antenna assemblies 402 which include antennas 402a, 402b and 402c, 402d respectively. As shown in FIG. 4A, antenna assemblies 402 are shunted to metallic plates 309 and 313 via a shunt 404. Shunt 404 may be composed of a metal such as copper, aluminum, stainless steel and may be formed as metal strips or foil. Alternatively, antenna 402 may be extended to metal plates 309 and 313. When antenna assemblies 402 are shunted to the ground-shield, the length $l_2$ of antennas 402a-402d and shunt 404 are odd multiples of a quarter wavelength (i.e. $\lambda/4$, $3\lambda/4$, $5\lambda/4$, etc.)

When the length $l_2$ is an odd multiple of a quarter wavelength, the wave terminates correctly and there is no mismatch, or voltage potential, at the shielding members 304 and 306. The maximum voltage potential would be in the middle of the jaw. If the length $l_2$ is not an odd multiple of a quarter wavelength, there will be a reflective wave. This could be utilized to move the peak voltage along the jaw members 410 and 420 by changing the frequency.

The Z distance between antenna assemblies (e.g., FIG. 3C, antenna assemblies 302) is not as critical as the length of the antenna assemblies. The Z distance will create some amplitude difference between the two jaw members but it won't affect the wavelength. This mismatch may be compensated for by the splitter 222.

Figure 5A:
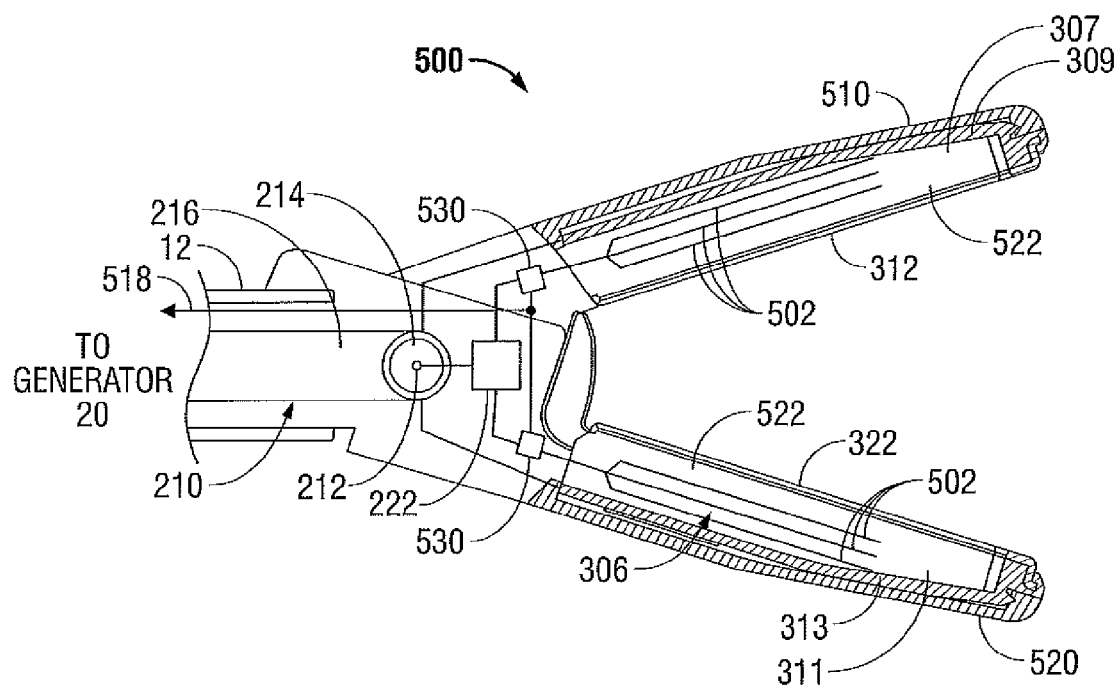
FIGS. 5A-5B are views of a microwave end effector assembly according to another embodiment of the present disclosure.
Figure 5B:
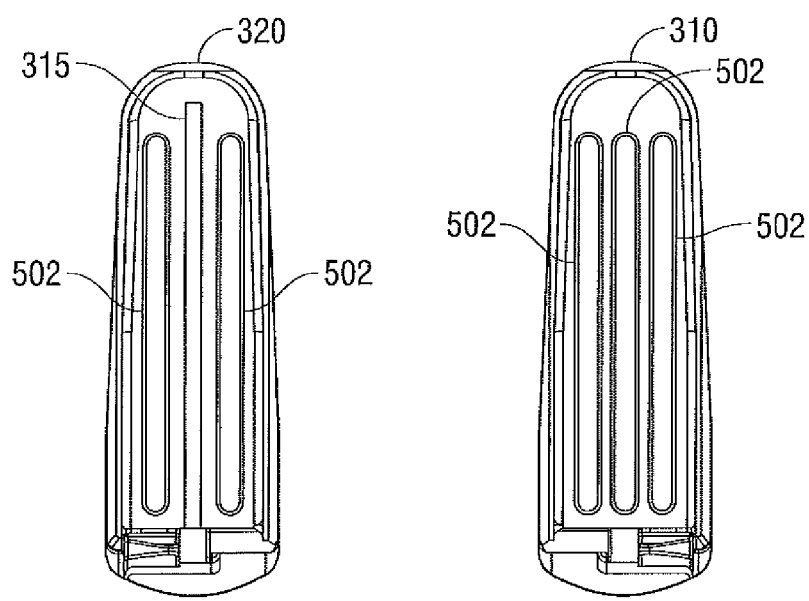

FIGS. 5A and 5B illustrate a microwave end effector assembly 500 according to another embodiment of the present disclosure. The end effector assembly 500 includes an antenna array in jaw members 510 and 520 that includes antennas 502. A multiplexer 530 is coupled between splitter 222 and antennas 502 in each jaw member 510 and 520. Both multiplexers 530 are operatively coupled to generator 20 via transmission line 518. Multiplexers 530 are used to select one or more of antennas 502 to vary the effective length of the antenna arrays. Each antenna 502 has a length that is a multiple of a half wavelength (i.e., $\lambda/2$, $\lambda$, $1.5\lambda$, $2\kappa$, etc.).

Figure 6:
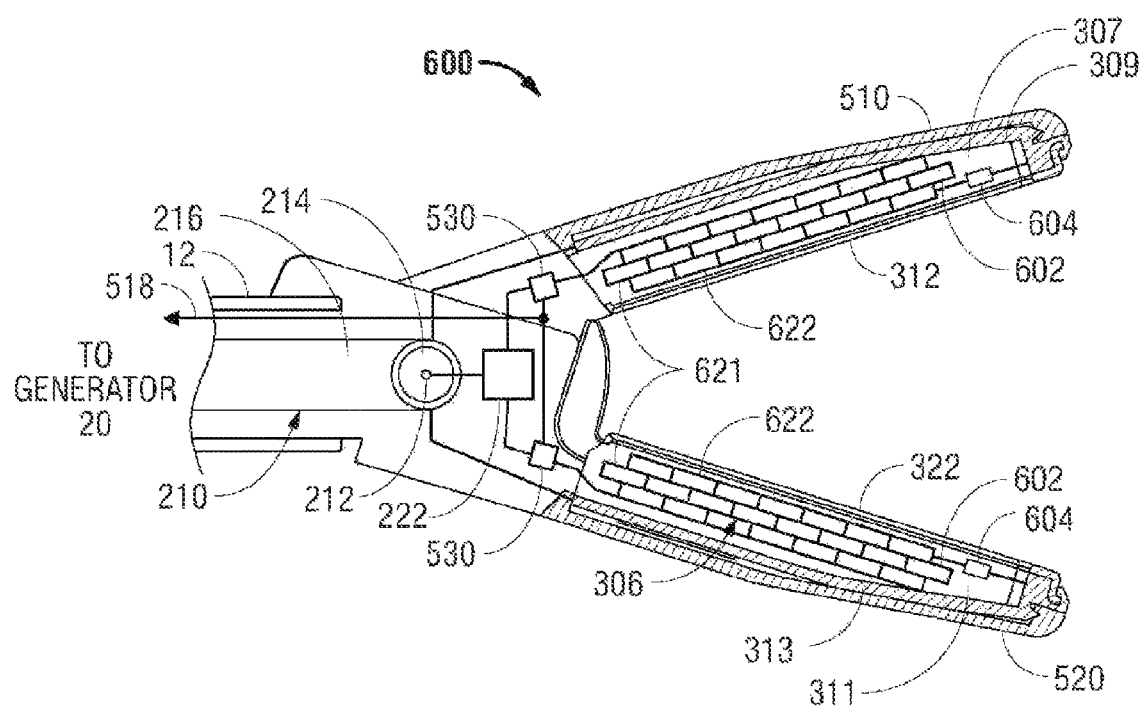
FIG. 6 is a view of a microwave end effector assembly according to another embodiment of the present disclosure.

FIG. 6 illustrates a microwave end effector assembly 600 according to another embodiment of the present disclosure. Assembly 600 includes an antenna assembly 602 where the proximal antenna 621 and each antenna 622 is shunted to the ground-shield via shunt 604. The length of proximal antenna 621 is an odd multiple of a quarter wavelength (i.e. $\lambda/4$, $3\lambda/4$, $5\lambda/4$, etc.) while each antenna 622 has a length that is a multiple of a half wavelength (i.e., λ/2, λ, 1.5λ, 2λ, etc.). Multiplexer 530 is used to select one or more of antennas 621 and/or 622.

Although the figures depict jaw members that are pivotable with respect to one another, the microwave antenna assemblies may be integrated into a pair of jaw members that move in parallel, either unilaterally or bilaterally, with respect to each other.

The foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing Figs. are presented only to demonstrate certain examples of the disclosure. Other elements, steps, methods and techniques that are insubstantially different from those described above and/or in the appended claims are also intended to be within the scope of the disclosure.

What is claimed is:

1. An end effector assembly for a microwave forceps, comprising:
   a pair of opposing jaw members, at least one jaw member is movable from a first position in spaced relation relative to the other jaw member to at least one subsequent position wherein the jaw members cooperate to grasp tissue therebetween, each of the jaw members including a microwave antenna assembly capable of generating an electromagnetic field and a shielding member including a metallic plate coupled to ground, a sealing surface, and a dielectric material, wherein the microwave antenna assembly is spaced apart from the sealing surface; and
   a splitter configured to receive an active signal from a source of microwave energy and split the active signal into a first signal transmitted to the microwave antenna assembly in one of the jaw members and a second signal transmitted in the microwave antenna assembly in the other jaw member.

2. The end effector assembly according to claim 1, wherein a phase of the first signal is offset in relation to a phase of the second signal.

3. The end effector assembly according to claim 2, wherein a phase of the first signal is offset by 180° in relation to a phase of the second signal.

4. The end effector assembly according to claim 1, wherein a distal end of the antenna assembly is terminated with an open.

5. The end effector assembly according to claim 4, wherein a length of the antenna assembly is a multiple of a half wavelength.

6. The end effector assembly according to claim 4, wherein a length of the antenna assembly is an odd multiple of a quarter wavelength.

7. The end effector assembly according to claim 1, wherein a distal end of the antenna assembly is shunted to ground.

8. An end effector assembly for a microwave forceps, comprising:
   a splitter configured to receive an active signal from a source of microwave energy and split the active signal into a first signal and a second signal;
   a pair of opposing jaw members, at least one jaw member is movable from a first position in spaced relation relative to the other jaw member to at least one subsequent position wherein the jaw members cooperate to grasp tissue therebetween, each of the jaw members including:
      a microwave antenna array having a first antenna and a plurality of second antennas and generating an electromagnetic field;
      a shielding member including a metallic plate of each jaw member coupled to ground, a sealing surface, and a dielectric material, wherein the microwave antenna array is spaced apart from the sealing surface; and
   a multiplexer configured to receive the first signal or the second signal from the splitter, wherein the multiplexer provides the first signal or the second signal to the first antenna or the first antenna and at least one of the plurality of second antennas in the microwave antenna array.

9. The end effector assembly according to claim 8, wherein a phase of the first signal is offset in relation to a phase of the second signal.

10. The end effector assembly according to claim 8, wherein a phase of the first signal is offset by 180° in relation to a phase of the second signal.

11. The end effector assembly according to claim 8, wherein the first antenna and each of the plurality of second antennas is terminated with an open.

12. The end effector assembly according to claim 11, wherein a length of the first antenna and each of the plurality of second antennas is a multiple of a half wavelength.

13. The end effector assembly according to claim 8, wherein the first antenna and each of the plurality of second antennas is shunted to ground.

14. The end effector assembly according to claim 13, wherein a length of the first antenna is an odd multiple of a quarter wavelength.

15. The end effector assembly according to claim 13, wherein a length of each of the plurality of second antennas is a multiple of a half wavelength.

* * * * *